United States Patent [19]

Klemarczyk et al.

[11] 4,390,464
[45] Jun. 28, 1983

[54] METHYL SUBSTITUTED NORBORNANE DERIVATIVES, ORGANOLEPTIC USES THEREOF AND PROCESS FOR PREPARING SAME

[75] Inventors: Philip T. Klemarczyk, Old Bridge; James M. Sanders, Eatontown; Manfred H. Vock, Locust; Joaquin F. Vinals, Rumson; Frederick L. Schmitt, Holmdel; Edward J. Granda, Englishtown, all of N.J.

[73] Assignee: International Flavors & Fragrances Inc., New York, N.Y.

[21] Appl. No.: 366,091

[22] Filed: Apr. 6, 1982

Related U.S. Application Data

[60] Division of Ser. No. 284,108, Jul. 16, 1981, Pat. No. 4,346,243, which is a continuation-in-part of Ser. No. 247,323, Mar. 25, 1981, Pat. No. 4,326,998, which is a continuation-in-part of Ser. No. 152,187, May 22, 1980, Pat. No. 4,284,824.

[51] Int. Cl.³ .............................. A61K 7/46; C11B 9/00
[52] U.S. Cl. .................................................. 252/522 R
[58] Field of Search ................... 252/522 R; 260/464

[56] References Cited

U.S. PATENT DOCUMENTS

| | | | |
|---|---|---|---|
| 3,304,167 | 2/1967 | Buntin et al. | 260/464 X |
| 3,492,330 | 1/1970 | Trecker et al. | 260/464 X |
| 3,928,247 | 12/1975 | Mookherjee et al. | 252/522 R |
| 3,956,355 | 5/1976 | Ueshima et al. | 260/464 |
| 4,146,507 | 3/1979 | De Simone | 252/522 R |
| 4,239,707 | 12/1980 | Mulder et al. | 260/464 X |

FOREIGN PATENT DOCUMENTS 54-22353  2/1979  Japan ................................. 260/464

*Primary Examiner*—Helen M. S. Sneed
*Attorney, Agent, or Firm*—Arthur L. Liberman

[57] ABSTRACT

Described are methyl substituted norbornane derivatives having the generic structure:

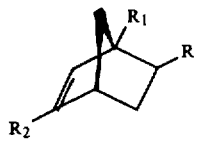

wherein R represents the nitrile moiety having the structure:

$$+C\equiv N]$$

or the dimethoxymethyl moiety having the structure:

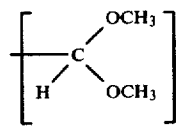

and wherein one of $R_1$, or $R_2$ is methyl and the other of $R_1$ or $R_2$ is hydrogen.

Also described are processes and compositions for augmenting or enhancing the flavor and/or aroma of consumable materials including foodstuffs, chewing gums, medicinal products, toothpastes, chewing tobaccos, perfumes, colognes and perfumed articles such as solid or liquid anionic, cationic, nonionic or zwitterionic detergents or fabric softeners or fabric softener articles using as the essential ingredient at least one of methyl substituted norbornane derivatives of our invention.

1 Claim, 6 Drawing Figures

FIG.I

GLC PROFILE FOR EXAMPLE I

FIG. 2 NMR SPECTRUM FOR FRACTION 3 OF EXAMPLE I.

IR SPECTRUM FOR FRACTION 3 OF EXAMPLE I

GLC PROFILE FOR EXAMPLE II

IR SPECTRUM FOR FRACTION II OF EXAMPLE II.

METHYL SUBSTITUTED NORBORNANE DERIVATIVES, ORGANOLEPTIC USES THEREOF AND PROCESS FOR PREPARING SAME

This is a divisional of application Ser. No. 284,108 filed July 16, 1981 which, in turn, is a continuation-in-part of application for United States Letters Patent, Ser. No. 247,323 filed on Mar. 25, 1981 which, in turn, is a continuation-in-part of application for United States Letters Patent, Ser. No. 152,187 filed on May 22, 1980, now U.S. Pat. No. 4,284,824 issued on Aug. 18, 1981.

BACKGROUND OF THE INVENTION

This invention provides novel methyl substituted norbornane derivatives having a generic structure:

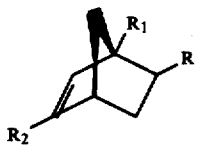

wherein R represents the nitrile moiety having the structure:

or the dimethoxymethyl moiety having the structure:

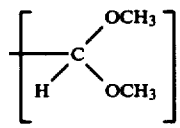

and wherein one of $R_1$, or $R_2$ is methyl and the other of $R_1$ or $R_2$ is hydrogen.

Materials which can provide jasmine/fruity, floral, chrysanthemum-like, calamus-like, camphoraceous, green, labdanum-like, castorium-like and leathery aromas are known in the art of perfumery. Many of the natural substances which provide such fragrances and contribute the desired nuances to perfumery compositions are high in cost, vary in quality from one batch to another and/or are generally subject to the usual variations of natural products.

By the same token, materials which can provide blueberry-like, sweet, coconut, macaroon-like (cooked coconut), hay-like, coumarin-like and green aroma and taste nuances are well-known in the art of flavoring for foodstuffs, toothpastes, chewing gums and medicinal products. Many of the natural materials which provide such flavor notes and contribute desired nuances to flavor and to flavor compositions are high in cost, vary in quality from one batch to another and/or are generally subject to the usual variations of natural products.

There is, accordingly, a continuing effect to find synthetic materials which will replace, enhance or augment the essential flavor and fragrance notes provided by natural essential oils or compositions thereof. Unfortunately, many of these synthetic materials have the desired nuances only to a relatively small degree or else contribute undesirable or unwanted odor to the compositions. The search for materials which can provide a more refined blueberry flavor or coconut flavor, for example, has been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural flavoring agents such as extracts, concentrates and the like are often subject to wide variations due to changes in quality, type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, ice cream desserts and yogurt desserts and the like are apt to be stored prior to use.

The fundamental problem in creating artificial flavor agents is that the artificial flavor to be achieved be as natural as possible. This generally proves to be a difficult task since the negativism for flavor development in many foods, medicinal products, chewing gums and toothpastes is not completely known. This is noticeable in products having blueberry flavor characteristics and coconut flavor characteristics, particularly.

Even more desirable are products that can serve to substituted for difficult-to-obtain natural perfumery oils and at the same time substitute for natural flavoring agents in foodstuffs, chewing gums, medicinal products and toothpastes.

The prior art contains a large number of teachings wherein compounds having the nitrile moiety or compounds having the dimethoxymethyl moiety or compounds having the norbornane moiety are useful in augmenting or enhancing the organoleptic properties of consumable materials. However, nothing in the prior art discloses the use for its organoleptic properties of any of the compounds defined according to the generic structure:

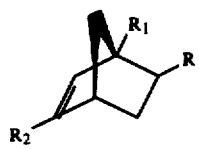

wherein R represents the nitrile moiety having the structure:

or the dimethoxymethyl moiety having the structure:

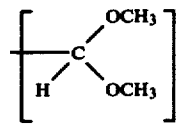

and wherein one of $R_1$, or $R_2$ is methyl and the other of $R_1$ or $R_2$ is hydrogen.

The prior art does show a compound having an aldehydic type structure which is patentably distinct from the instant structures, as an intermediate for producing compounds having organoleptic properties useful in augmenting or enhancing the aroma or taste of consumable materials. Thus, U.S. Pat. No. 4,143,074 in Example I discloses the use as an intermediate for preparing alcohols and ketones, the compound having the structure:

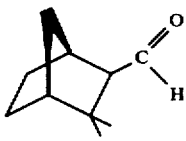

This compound is different in kind, in structure and in properties from the compounds defined according to the generic structure:

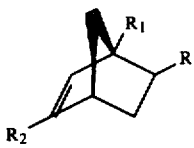

wherein R represents the nitrile moiety having the structure:

or the dimethoxymethyl moiety having the structure:

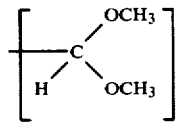

and wherein one of $R_1$, or $R_2$ is methyl and the other of $R_1$ or $R_2$ is hydrogen.

U.S. Pat. No. 3,067,244 issued on Dec. 4, 1962 discloses interalia Diels-Alder reaction products of conjugated dienes including cyclopentadiene (at column 1, line 64 with alpha, beta unsaturated alkanols (at column 2, line 15) having the structure:

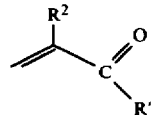

wherein $R^1$ represents one of hydrogen, hydroxyl or alkyl and $R^2$ represents hydrogen, carboxcyclic acid or alkyl. Included in the large list of unsaturated alkanols is acrolein at column 2, line 42. Disclosed also in U.S. Pat. No. 3,067,244 is the process involving reaction of the conjugated diene and dienophile using Lewis acids including aluminum diethylchloride and aluminum ethyl dichloride but also including other Lewis acids, titanium tetrachloride, stannic chloride, aluminum trichloride, ferric chloride, zinc chloride and boron trifluoride.

The reaction involving *methyl cyclopentadienes* and unsaturated dienophiles such as acrylo nitrile and 1,1-dimethoxypropen-2, however, is not disclosed in U.S. Pat. No. 3,067,244 nor are the unobvious, unexpected and advantageous organoleptic properties of the resultant products suggested in U.S. Pat. No. 3,067,244.

Indeed, there is no suggestion that in the reaction of the methyl cyclopentadienes and the unsaturated compounds of our invention, only ethyl aluminum dichloride and aluminum diethylchloride and their corresponding bromides will be usable as catalysts for the reaction, the other "catalysts" listed at 51-55 of column 2 of U.S. Pat. No. 3,067,244 not being workable for the reactions of our invention. Indeed, in a paper published at page 249 of the Jan. 5, 1961 issue of the Journal of American Chemical Society entitled "Catalysts of the Diels-Alder Reaction" by Fray & Robinson, the inventors on U.S. Pat. No. 3,067,244, it was further mentioned that "In comparative experiments with methylvinylketone and titamium tetrachloride . . . cyclopentadiene yielded only polymer and dimer respectively . . . ".

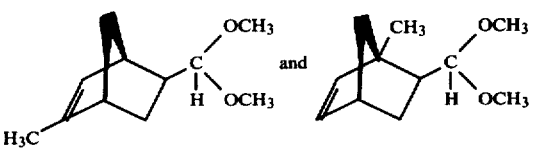

Figure 2:
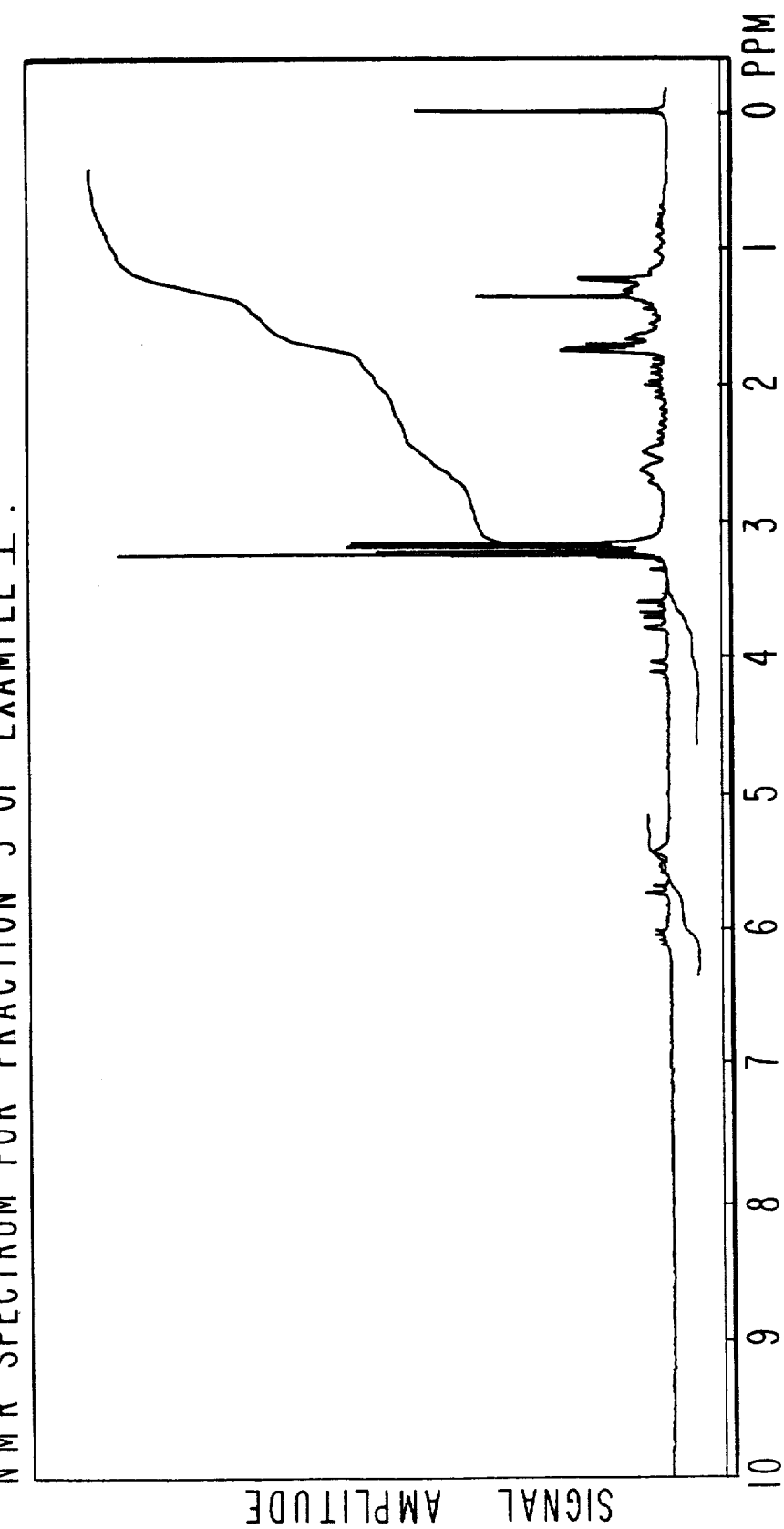

FIG. 2 represents the NMR spectrum for fraction 3 of the distillation product of the reaction product of Example I containing the compounds having the structures:

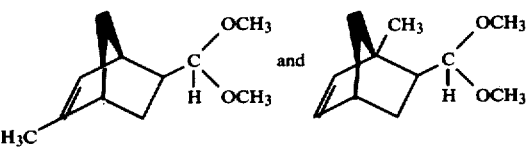

Figure 3:
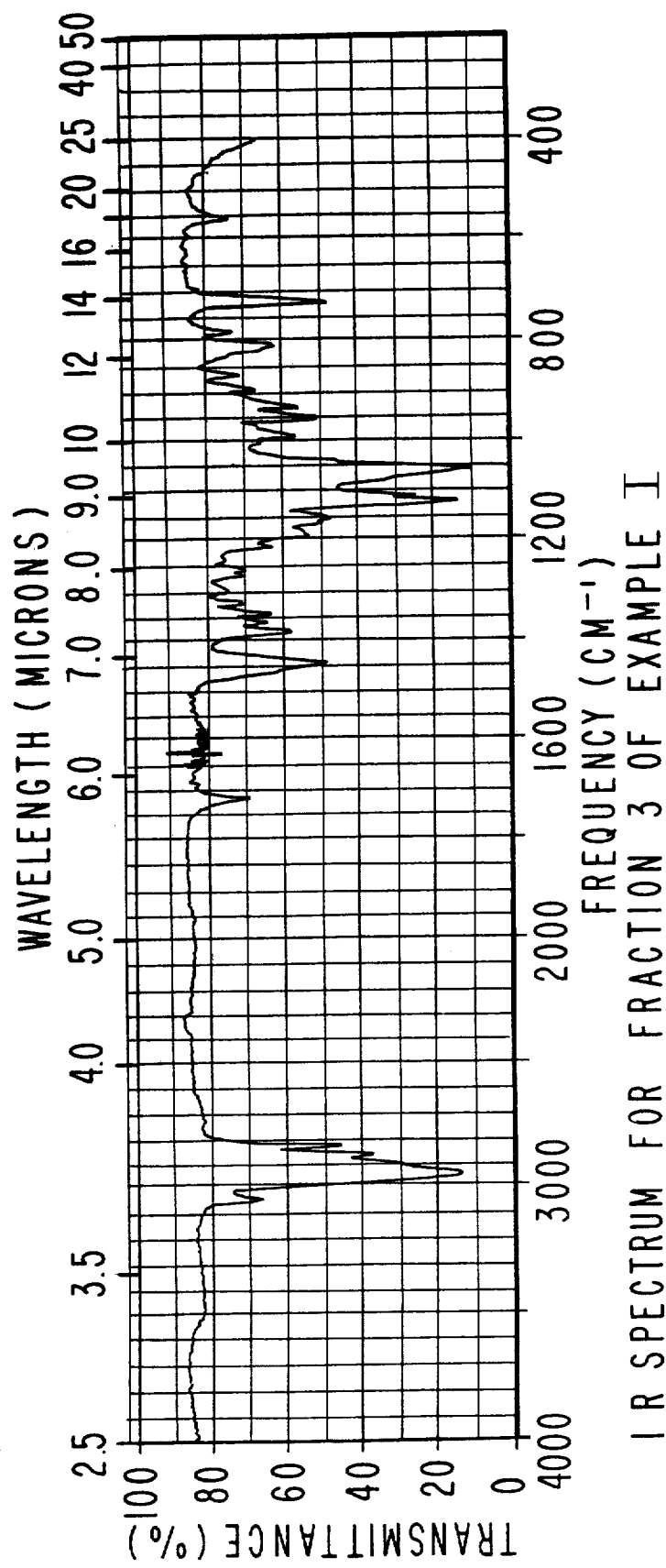

FIG. 3 represents the infra-red spectrum for fraction 3 of the distillation product of the reaction product of Example I containing the compounds having the structures:

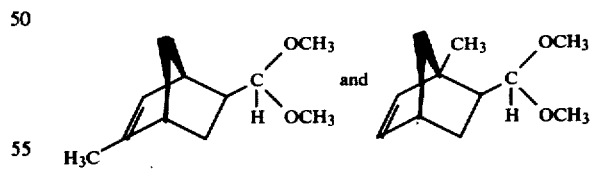

Figure 4:
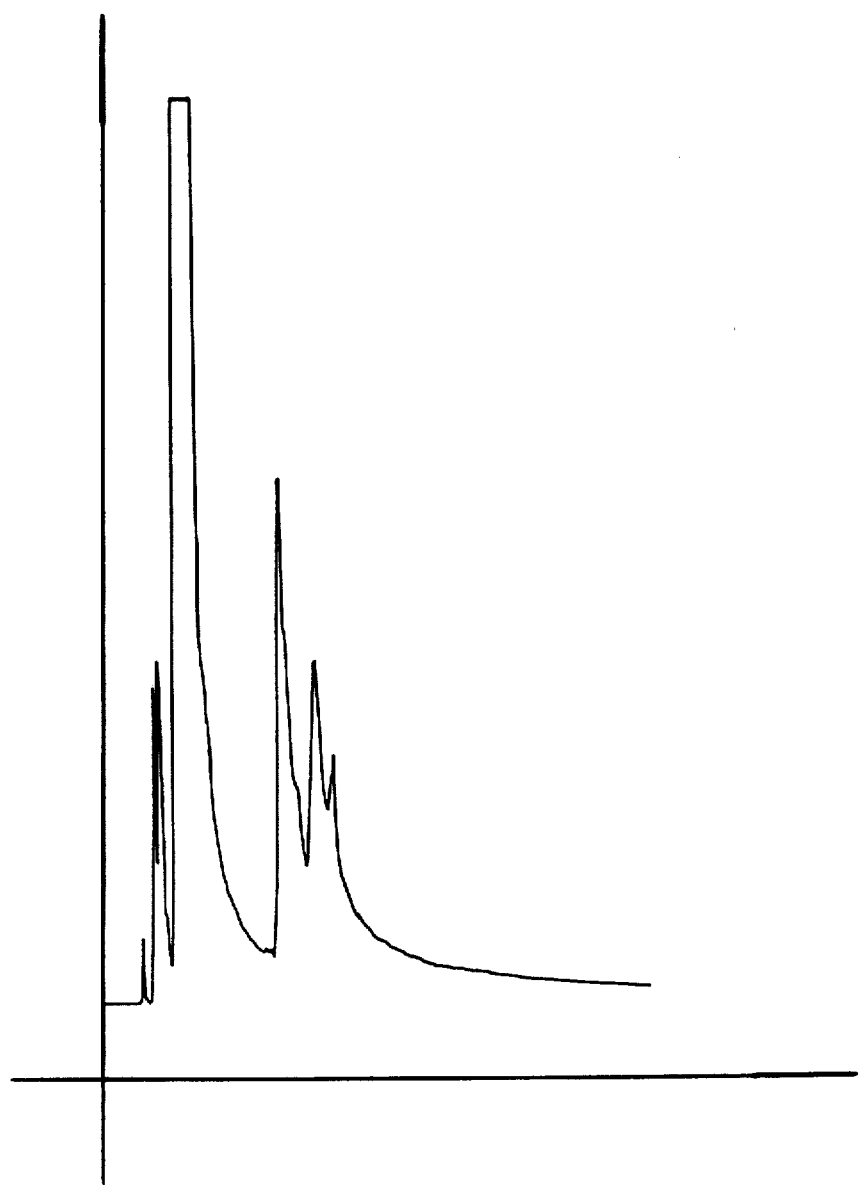

FIG. 4 sets forth the GLC profile for the reaction product of Example II containing the compounds having the structures:

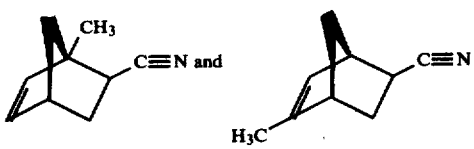

Figure 5:
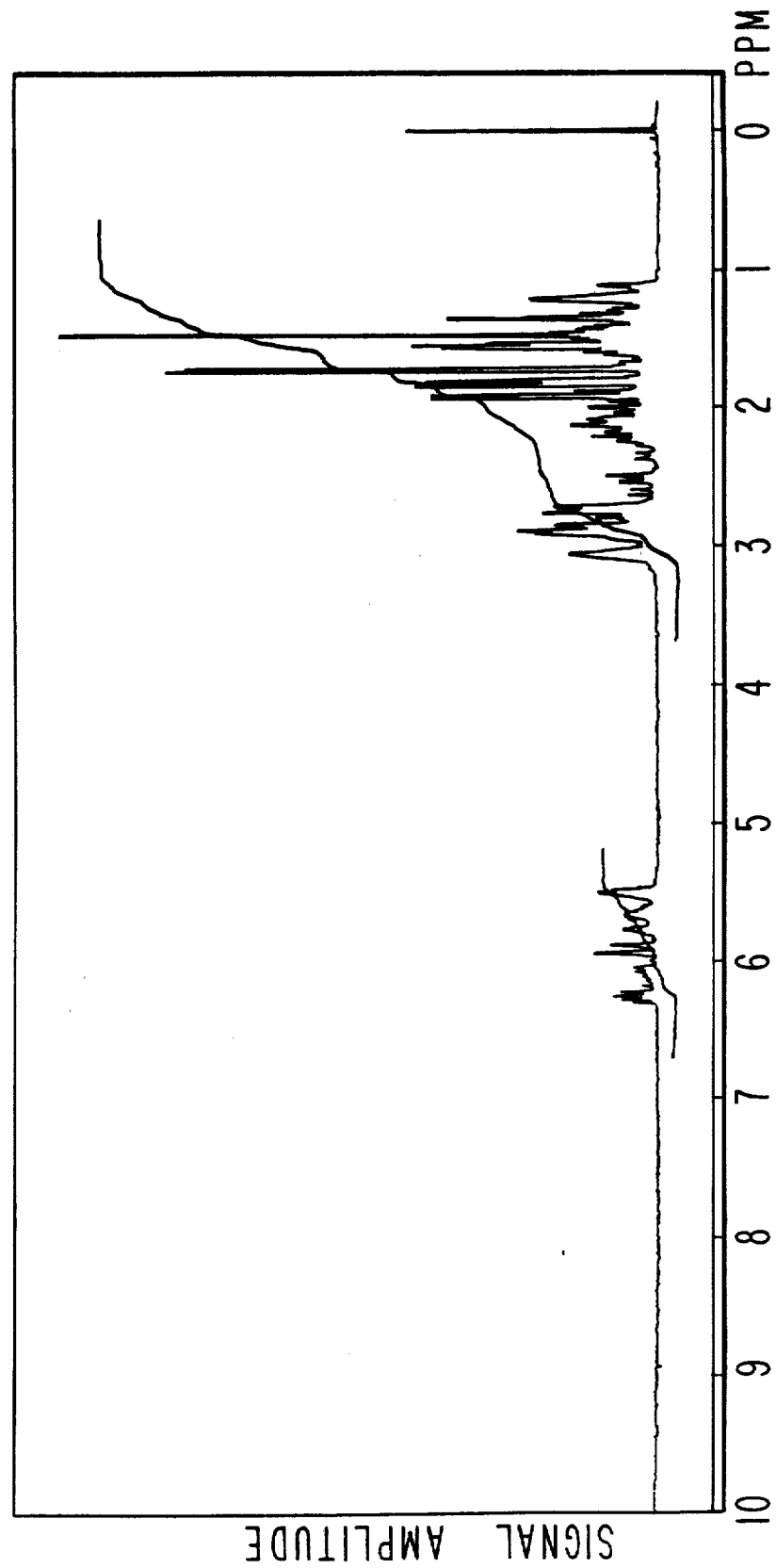

FIG. 5 is the NMR spectrum for fraction 11 of the distillation product of the reaction product of Example II containing the compounds having the structures:

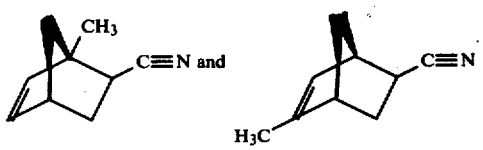

Figure 6:
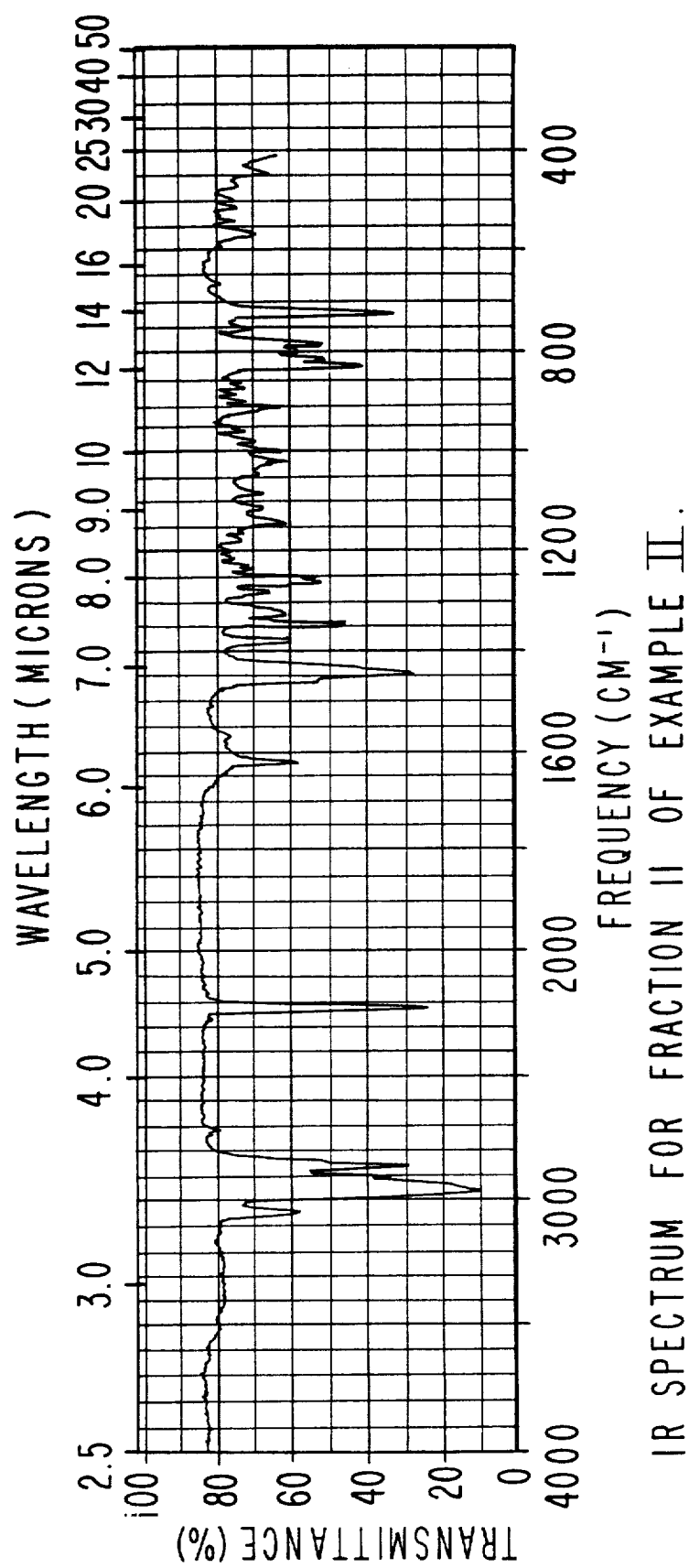

FIG. 6 is the infra-red spectrum for fraction 11 of the distillation product of the reaction product of Example II containing the compounds having the structures:

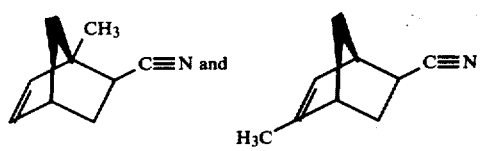

THE INVENTION

The present invention provides the compounds defined according to the generic structure:

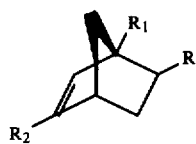

wherein R represents the nitrile moiety having the structure:

or the dimethoxymethyl moiety having the structure:

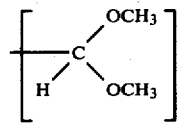

and wherein one of $R_1$, or $R_2$ is methyl and the other of $R_1$ or $R_2$ is hydrogen.

The present invention also provides an economical efficient process for synthesizing the compounds defined according to the generic structure:

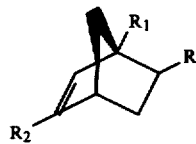

wherein R represents the nitrile moiety having the structure:

or the dimethoxymethyl moiety having the structure:

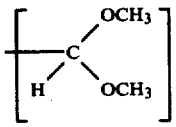

and wherein one of $R_1$, or $R_2$ is methyl and the other of $R_1$ or $R_2$ is hydrogen, by reacting an unsaturated nitrile, acrylo nitrile or 1,1-dimethoxypropene-2 with a mixture of 1-methyl-1,3-cyclopentadiene and 2-methyl-1,3-cyclopentadiene freshly produced from the process of cracking methyl cyclodiene dimer.

The present invention also provides processes for utilizing the compounds defined according to the generic structure:

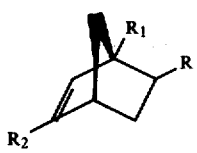

wherein R represents the nitrile moiety having the structure:

or the dimethoxymethyl moiety having the structure:

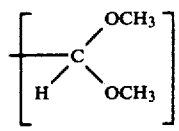

and wherein one of $R_1$, or $R_2$ is methyl and the other of $R_1$ or $R_2$ is hydrogen, for their organoleptic properties in augmenting or enhancing the organoleptic properties of consumable materials, that is, the aroma or taste of perfumes, colognes, perfumed articles (such as solid or liquid anionic, cationic, nonionic or zwitterionic detergents, soaps, fabric softener compositions, dryer-added fabric softener articles such as "BOUNCE ®", a registered trademark of the Procter & Gamble Company of Cincinnati, Ohio, fabric brighteners and cosmetic powders), food flavor compositions, foodstuffs, chewing gums, toothpastes, chewing tobaccos and medicinal products particularly those having blueberry flavors or coconut flavors.

The substituted norbornane derivatives of our invention may be prepared by first reacting an unsaturated compound having the generic structure:

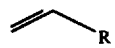

wherein R represents one of the moieties:

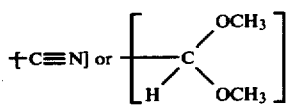

with 1-methyl-1,3-cyclopentiene having the structure:

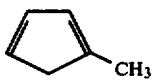

or a mixture of 1- and 2-methyl-1,3-cyclopentadiene signified by the structure:

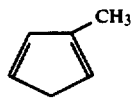

which are all freshly prepared from cracking methylcyclopentadiene dimer by passing the methyl cyclopentadiene dimer through a distillation column at 175° C. which distillation column is packed preferably with Berle Saddles or Raschig Rings. The reaction of the methyl cyclopentadiene(s) with the unsaturated derivative having the structure:

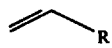

takes place at a temperature of between 0° C. and 50° C. and in the presence of a alkyl aluminum halide catalyst having the structure:

wherein R' is $C_1$–$C_3$ alkyl, preferably ethyl; X is chloro or bromo; m+n=3 with m being 1 when n is 2 and m being 2 when n is 1. The reaction preferably takes place in the presence of a solvent such as toluene.

The products of the reaction are compounds having the generic structure:

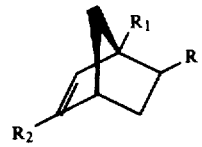

wherein R represents the nitrile moiety having the structure:

or the dimethoxymethyl moiety having the structure:

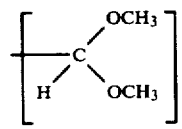

and wherein one of $R_1$, or $R_2$ is methyl and the other of $R_1$ or $R_2$ is hydrogen. The resulting products can be used in admixture for their organoleptic properties; or they can be separated as by fractional distillation to yield raw materials which can be used for their organoleptic properties.

On the other hand, compounds defined according to the structure:

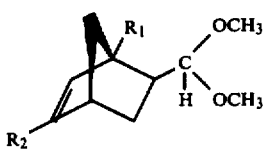

(wherein one of $R_1$ or $R_2$ is methyl and the other of $R_1$ or $R_2$ is hydrogen or mixtures of same) may be prepared by reacting the corresponding aldehyde defined according to the structure:

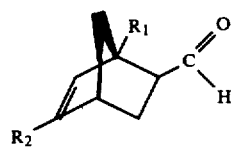

(wherein one of $R_1$ or $R_2$ is methyl and the other of $R_1$ or $R_2$ is hydrogen) prepared according to, for example, Example I of application for United States Letters Patent, Ser. No. 247,323 filed on Mar. 25, 1981, in the presence of an alkali metal alkoxide and in the presence of a lower alkanol. The most suitable of the alkali metal alkoxides is sodium metholate, $NaOCH_3$, and the most suitable alcohol and most economical and convenient is methanol. Thus, exemplary of the reaction which may take place to form the group of compounds defined according to structure:

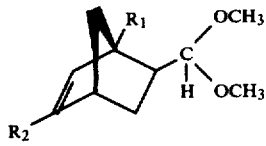

is the following reaction:

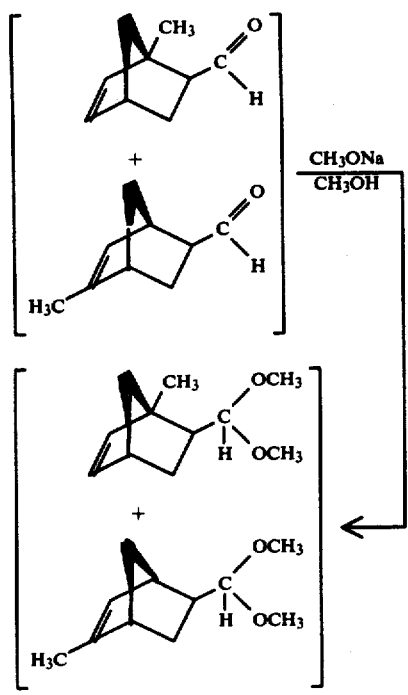

The reaction is preferably carried out under reflux conditions, conveniently at atmospheric pressure. At the end of the reaction, the reaction product may be fractionally distilled in vacuo to yield the desired and useful dialkoxy derivative defined according to the structure:

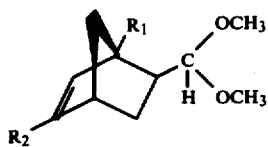

The resulting material may be separated into its isomeric components as by high pressure liquid chromatography techniques.

Examples of the products formed according to our invention and their organoleptic properties are as follows:

TABLE I

| Structure of Norbornane Derivative of our Invention | Flavor Properties | Fragrance Properties |
|---|---|---|
| Mixture of compounds prepared according to Example I, infra, containing the compounds having the structures: 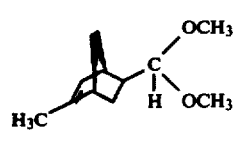 and | A blueberry aroma and 0.05 ppm. | A floral, chrysanthemum and calamus-like aroma with camphoraceous, green, labdanum-like, castorium-like and leathery notes on dry-out. |

TABLE I-continued

| Structure of Norbornane Derivative of our Invention | Flavor Properties | Fragrance Properties |
|---|---|---|
| Mixture of compounds prepared according to Example II, infra, containing the compounds having the structures: and | A sweet, coconut-like, macaroon-like, (cooked coconut) hay-like, coumarin-like and green aroma and taste profile at 1 ppm. | A jasmine/fruity aroma. |

When the substituted norbornane derivatives of our invention are used as food flavor adjuvants, the nature of the co-ingredients included with the substituted norbornane derivatives of our invention used in formulating the product composition will also serve to alter, modify, augment or enhance the organoleptic characteristics of the ultimate foodstuff treated herewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "Foodstuff" includes both solid and liquid ingestible materials which usually do, but need not have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible nontoxic materials which have medicinal value such as cough syrups, cough drops, aspirin and chewable medicinal tablets.

The term "chewing gum" is intended herein to mean a composition which comprises a substantially water-insoluble, chewable plastic gum base such as chickle, or substitutes therefor, including julutong, quttakay, rubber or certain cosmetible natural or synthetic resins or waxes. Incorporated with the gum base in admixture therewith may be plasticizers or softening agents, e.g., glycerine, and a flavoring composition which incorporates one or more of the substituted norbornane derivatives of our invention and, in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious, particularly from an organoleptic standpoint whereby the ultimate flavor and/or aroma of a consumable material used is not caused to have unacceptable aroma and taste nuances. Such materials may in general be characterized as flavoring agents or vehicles comprising broadly, stabilizers, thickeners, surface agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth, gelatin, proteinaceous materials, lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous glyconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid and 2-methyl-cis-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,-beta-dimethyl-acrolein, methyl-n-amyl ketone, n-hexanal, iso-pentanal, hydrocinnamic aldehyde, dis-3-hexenal, 2-heptanal, n-nonyl-aldehyde, 4-(p-hydroxyphenyl)-2-butanone, alpha-ionone, beta-ionone, methyl-3-butanone, benzaldehyde, β-damascone, β-damascenone, acetophone, 2-heptanone, o-hydroxyacetophone, 2-methyl-2-hepten-6-one, 2-octanone, 2-undecanone, 3-phenyl-4-pentenal, 2-phenyl-2-hexanal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin, esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, isoamyl acetate, isopropyl butyrate, methyl acetate, methyl butytrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, n-dodecane, methyl diphenyl, methyl naphthalene, mycrene, naphthalene, n-octadecane, n-tetradecane, tetramethyl naphthalene, n-tridecane, trimethyl naphthalene, undecane, caryophyllene, 1-phellandrene, p-cymene and 1-alpha-pimene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, 2-isopropyl-4,5-dimethylpyrazine, 1-methyl-2-ethylpyrazine, tetramethylpyrazine, trimethylpyrazine, essential oils, such as jasmine absolute, cassia oil, cinnamon bark oil, rose absolute, orris absolute, lemon essential oil, Bulgarian rose, coconut oil, coconut oil extract, yara yara and vanilla, lactones such as delta nonalactone, gamma nonalactone, delta dodecalactone, gamma dodecalactone, sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the substituted norbornane derivatives of our invention by not covering or spoiling the organoleptic properties (aroma and/or taste) thereof; (ii) be non-reactive with the substituted norbornane derivatives of our invention and (iii) be capable of providing an environment in which the substituted norbornane derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the substituted norbornane derivatives employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavor composition.

The use of insufficient quantities of substituted norbornane derivatives will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing compositions, medicinal product compositions and toothpaste compositions, it is found that quantities of substituted norbornane derivatives ranging from a small but effective amount, e.g., 0.02 parts per million up to about 300 parts per million based on total composition are suitable. Concentrations in excess of the maximum quantity stated are not normally recommended, since they fail to provide commensurate enhancement of organoleptic properties. In those instances, wherein substituted norbornane derivatives are added to the foodstuff as an integral component of a flavoring composition, it is, of course, essential that the total quantity of flavoring composition employed be sufficient to yield an effective concentration of substituted norbornane derivatives in the foodstuff product.

Food flavoring compositions prepared in accordance with the present invention preferably contain substituted norbornene derivatives in concentrations ranging from about 0.05% up to about 15% by weight on the total weight of the said flavoring composition.

The composition described herein can be prepared according to conventional techniques well known as typified by cake batters, fruit drinks and coconut drinks and alcoholic beverages (e.g., pina colada) and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing substituted norbornane derivatives with, for example, gum arabic, gum tragacanth, carrageenan and the like, and thereafter spray-drying the resultant mixture whereby to obtain the particularate solid product. Prepared flavor mixes in powder form, e.g., fruit flavored powder mixes are obtained by mixing the dried solid components e.g., starch, sugar and the like and one or more substituted norbornane derivatives in a dry blender until the requisite degree of uniformity is achieved.

It is presently preferred to combine with substituted norbornane derivatives of our invention the following adjuvants:
p-hyroxybenzyl acetone;
geraniol;
cassia oil;
acetaldehyde;
maltol;
ethyl methyl phenyl glycidate;
benzyl acetate;
dimethyl sulfide;
eugenol;
vanillin;
caryophyllene;
guaiacol;
ethyl pelargonate;
cinnamaldehyde;
methyl anthranilate;
5-methyl furfural;
isoamyl acetate;
isobutyl acetate;
cuminaldehyde;
alpha ionone;
cinnamyl formate;
ethyl butyrate;
methyl cinnamate;
acetic acid;
gamma-undecalactone;
gamma-dodecalactone;
delta-undecalactone;
delta-decalactone;
delta-dodecalactone;
naphthyl ethyl ether;
diacetyl;
furfural;
ethyl acetate;
anethole;
2,3-dimethyl pyrazine;
2-ethyl-3-methyl pyrazine;
3-phenyl-4-pentenal;
2-phenyl-2-hexanal;
2-phenyl-2-pentenal;
3-phenyl-4-pentenal diethyl acetal;
beta-damascone (1-crotonyl-2,6,6-trimethyl-cyclohex-1-ene);
beta-damascenone (1-crotonyl-2,6,6-trimethyl-cyclohexa-1,3-diene);
beta-cyclohomocitral (2,6,6-trimethylcyclohex-1-ene carboxaldehyde);
isoamyl butyrate;
cis-3-hexanol-1;
2-methyl-2-pentenoic acid;
elemecine (4-allyl-1,2,6-trimethyoxybenzene);
isoelemecine (4-propenyl-1,2,6-trimethoxybenzene); and
2-(4-hydroxy-4-methylpentyl) norbornadiene.

The methyl substituted norbornane derivatives of our invention can be used to contribute jasmine/fruity, camphoraceous, green, labdanum-like, castoreum-like, leathery, floral, chrysanthemum-like and calamus-like aromas to perfume compositions, perfumed articles such as solid or liquid anionic, cationic, nonionic or zwitterionic detergents, fabric softener compositions, fabric softener articles, fabric optical brighteners and other fabric conditioners. As olfactory agents the substituted norbornane derivatives of our invention can be formulated into or used as components or a "perfumed composition".

The term "perfumed composition" is used herein to mean a mixture of organic compounds including, for example, alcohols, aldehydes, ketones, nitriles (other than the methyl substituted norbornane and nitrile derivatives of our invention) ethers, (other than the acetals of our invention), lactones and frequently hydrocarbons which are admixed so that the combined odors of the individual components produce a pleasant or desired fragrance. Such perfume compositions usually contain (a) the main note of the "bouquet" or foundation stone of the composition; (b) modifiers which round off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of methyl substituted norbornane derivatives of our invention which will be effective in perfume compositions depends upon many factors including the other ingredients, their amounts and the effects which are desired. It has been found that perfume compositions containing as little as 1% of the methyl substituted norbornane derivatives of our invention or even less and perfume compositions containing as much as 70% of the methyl substituted norbornane derivatives of our invention can be used to impart interesting jasmine/fruity, camphoraceous, green, labdanum-like, castoreum-like, leathery, floral, chrysanthemum-like, and calamus-like aromas to perfumed articles, perfume compositions and colognes. Such perfumed articles include fabric softener compositions, dryer-added fabric softeners, cosmetic powders, talcs and solid or liquid anionic, cationic, nonionic or zwitterionic detergents. The amount employed can range up to 70% and will depend on considerations of cost, nature of the end product and the effect desired on the finished product and particular fragrance sought.

Thus, the methyl substituted norbornane derivatives of our invention can be used alone or in a perfume composition as an olfactory component in solid or liquid anionic, cationic, nonionic or zwitterionic detergents (including soaps), space odorants and deodorants; perfumes; colognes, toilet waters, bath salts, hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article such as a solid or liquid cationic, nonionic, anionic or zwitterionic detergent or of a cosmetic powder, as little as 0.01% of one or more of the methyl substituted norbornane derivatives of our invention will suffice to provide an interesting jasmine/fruity, camphoraceous, green, labdanum-like, castoreum-like, leathery, floral, chrysanthemum-like and calamus-like aroma. Generally, no more than 0.8% of the methyl substituted norbornane derivatives of our invention is required.

In addition, the perfume compositions of our invention can contain a vehicle or carrier for the methyl substituted norbornane derivatives of our invention alone or with other ingredients. The vehicle can be a liquid such as an alcohol, such as ethanol, a glycol such as propylene glycol, or the like. The carrier can be an absorbent solid such as a gum, or components for encapsulating the composition by coacervation.

The following Examples I and II set forth processes for preparing the methyl substituted norbornane derivatives of our invention as it is presently preferred to practice it.

EXAMPLE I

Preparation of the Dimethyl Acetal of 4(and 5)Methyl-5-norbornene-2-carboxaldehyde Reaction:

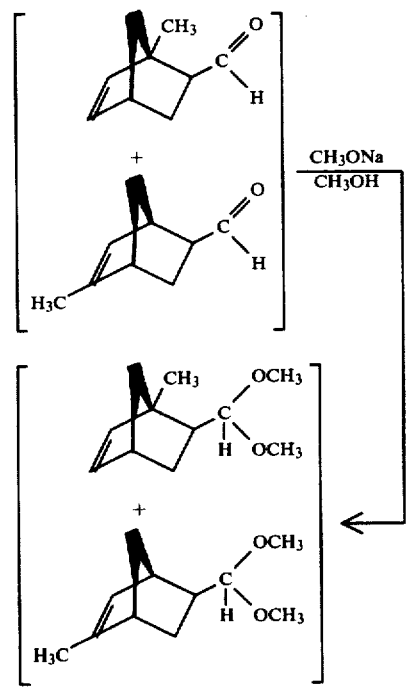

Into a one-liter reaction flask equipped with stirrer, condenser, thermometer is placed 8.64 grams (0.04 moles) of a solution of 25% sodium methylate in anhydrous methanol. Over a period of one hour through a dropping funnel, 115.0 grams (0.845 moles) of a mixture of aldehydes prepared according to Example I of application for U.S. Letters Patent, Ser. No. 247,323 filed on Mar. 25, 1981 is added, and this aldehyde is defined according to the structure:

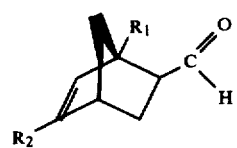

wherein in one of the molecules, $R_1$ is hydrogen and $R_2$ is methyl and in the other of the molecules of the mixture, $R_2$ is hydrogen and $R_1$ is methyl. The reaction mass exotherms to 30° C. after the addition. The reaction mass is then refluxed for a period of 4 hours while monitoring the progress of the reaction with a GLC apparatus. The reaction mass is then cooled to room temperature and 100 cc of water is added. The reaction mass is then extracted with 100 cc of toluene and the toluene extract is washed with two portions of 100 cc each of water. The resulting organic layer is then dried and stripped on a "Rushover" column. The distillation is carried out on a 12" stone-packed column yielding the following fractions:

| Fraction Number | Vapor Temp. (°C.) | Liquid Temp. (°C.) | Pressure mm/Hg. |
|---|---|---|---|
| 1 | 40/45 | 60/67 | 2.5/2.5 |
| 2 | 50 | 70 | 2.0 |
| 3 | 55 | 90 | 2.0 |
| 4 | 55 | 110 | 2.0 |

The resulting distillate is then redistilled on a micro vigreux column yielding the following fractions:

| Fraction Number | Vapor Temp. (°C.) | Liquid Temp. (°C.) | Pressure mm/Hg. |
|---|---|---|---|
| 1 | 45/50 | 50/60 | 2.0/2.0 |
| 2 | 50 | 60 | 2.0 |
| 3 | 50 | 63 | 2.0 |
| 4 | 50 | 63 | 2.0 |

Figure 1:
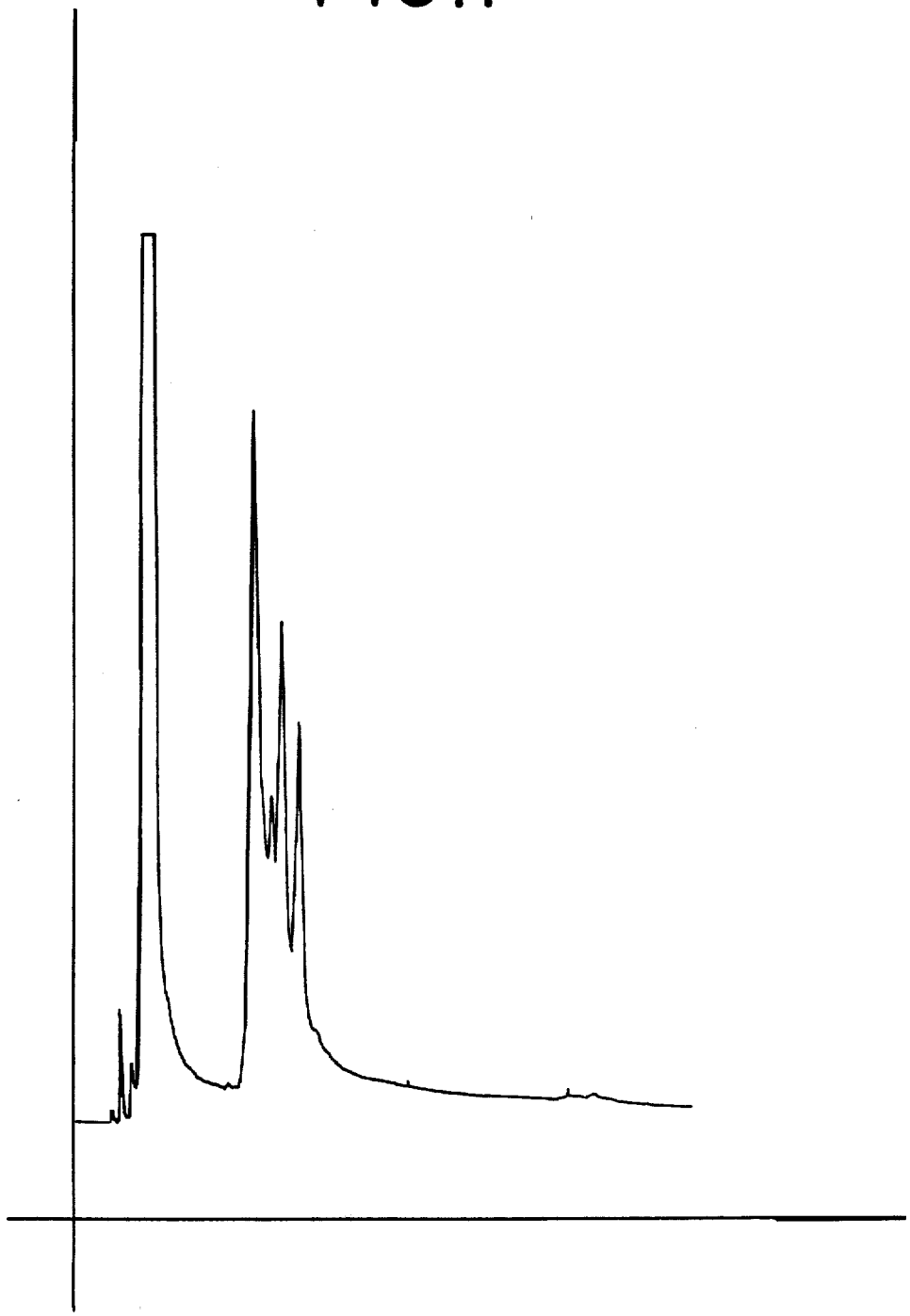
FIG. 1 sets forth the GLC profile at the end of one hour of reaction of the reaction product of Example I containing the compounds having the structures.

FIG. 1 is the GLC profile for the reaction product after one hour refluxing. (Conditions: SE-30 column programmed at 150°–200° C.).

FIG. 2 is the NMR spectrum for fraction 3 of the foregoing distillation.

FIG. 3 is the infra-red spectrum for fraction 3 of the foregoing distillation.

EXAMPLE II

Preparation of 5(and 6)-Methyl-5-norbornene-2-carbonitrile

Reaction:

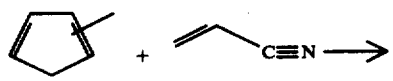

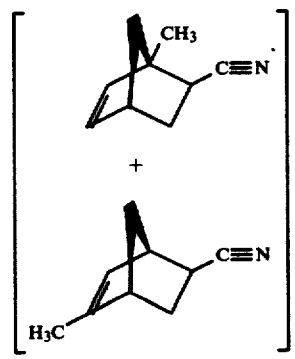

Into an autoclave is placed 640.0 grams (4.0 moles) of a 50% mixture of methyl cyclopentadiene (in toluene) prepared according to Example A of application for U.S. Letters Patent Ser. No. 247,323 filed on Mar. 25, 1981 and 212 grams (4.0 moles) of acrylo nitrile. The autoclave is sealed and the contents heated to 100°–100° C. for a period of 8 hours with shaking. GLC at the end of the 8 hour period shows completion of the reaction. The reaction mass is then distilled to give 469 grams of product (88% yield). The material is first distilled on a 12" stone packed column yielding the following fractions:

| Fraction Number | Vapor Temp. (°C.) | Liquid Temp. (°C.) | Pressure mm/Hg. |
|---|---|---|---|
| 1 | 95/100 | 105/110 | 10.0/10.0 |
| 2 | 105 | 115 | 10.0 |
| 3 | 110 | 115 | 10.0 |
| 4 | 110 | 116 | 10.0 |
| 5 | 110 | 180 | 10.0 |

The Rushed over distilled material is then redistilled on an 18" Goodloe column yielding the following fractions:

| Fraction Number | Vapor Temp. (°C.) | Liquid Temp. (°C.) | Pressure mm/Hg. |
|---|---|---|---|
| 1 | 35/60 | 110/110 | 15/15 |
| 2 | 100 | 115 | 15.0 |
| 3 | 100 | 120 | 15.0 |
| 4 | 120 | 128 | 15.0 |
| 5 | 120 | 128 | 15.0 |
| 6 | 120 | 128 | 15.0 |
| 7 | 120 | 130 | 15.0 |
| 8 | 115 | 120 | 15.0 |
| 9 | 117 | 125 | 15.0 |
| 10 | 120 | 125 | 15.0 |
| 11 | 118 | 125 | 15.0 |
| 12 | 118 | 125 | 15.0 |
| 13 | 118 | 125 | 15.0 |
| 14 | 118 | 169 | 15.0 |

Fractions 4–14 are bulked and utilized in the following examples.

FIG. 4 is the GLC profile for the reaction product after the initial distillation prior to the final fractional distillation (SE-30 column programmed at 150°–200° C. at 8° C. per minute).

FIG. 5 is the NMR spectrum for fraction 11 of the foregoing distillation.

FIG. 6 is the infra-red spectrum for fraction 6 of the foregoing distillation.

EXAMPLE III

The following leathery floral and herbal type formula is prepared:

| Ingredient | Parts by Weight |
|---|---|
| Geranium bourbon | 20.0 |
| Rosemary oil Spanish | 10.0 |
| Lavendar oil barreme | 10.0 |
| Thyme oil white | 10.0 |
| Amyl cinnamic aldehyde | 10.0 |
| Sauge sclaree French | 5.0 |
| Sandalwood oil | 5.0 |
| Galbanum oil | 5.0 |
| Patchouli oil light | 5.0 |
| Cedarwood oil light | 15.0 |

-continued

| Ingredient | Parts by Weight |
|---|---|
| Product produced according to Example I, bulked fractions 2-4 containing and consisting of the compounds having the structures: | 5.0 |

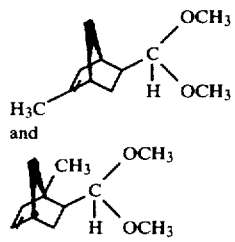
and

When the composition of matter prepared according to Example I is incorporated into the formula at 5%, the composition of matter adds a pleasant floral, chrysanthemum-like, calamus-like, leathery, castoreum-like, labdanum-like and camphoraceous undertone to this leathery, floral and herbal type formula.

EXAMPLE IV

A jasmine formula is produced containing the following ingredients:

| Ingredients | Parts by Weight |
|---|---|
| Isoeugenol | 2.0 |
| Benzyl propionate | 10.0 |
| Benzyl acetate | 13.0 |
| Benzyl alcohol | 14.0 |
| Benzyl benzoate | 9.0 |
| Linalool | 8.0 |
| Phytol | 30.0 |
| Methyl oleate | 4.0 |
| Methyl palmitate | 4.0 |
| Indol - 10% in diethyl phthalate | 1.0 |
| Composition produced according to Example II containing bulked fractions 4-14 and containing the compounds having the structures: | 5.0 |

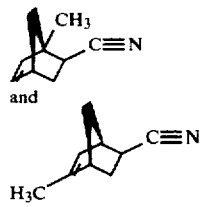
and

The material produced according to Example II incorporated into the formula above at 5.0% gives rise to the pleasant fruityness aroma undertone of this jasmine formulation.

EXAMPLE V

A stable lotion is prepared with the following formulation:

| Ingredients | Parts by Weight |
|---|---|
| Poly(N,N—dimethyl-3,5-dimethylene piperidinium chloride) (Merquat 100, Merck & Co., U.S.A., average molecular weight 50,000–100,000, viscosity in 40% aqueous solution, 10,000 cps.) | 1.0 |
| Cocoamidopropyl dimethyl glycine (betaine) | 5.7 |
| Myristyl dimethylamine oxide | 12.0 |
| Stearic monoethanolamide opacifier | 2.0 |
| Perfume as indicated in Table II (below) giving rise to the aroma profiles as indicated in Table II (below) | 0.5 |
| Water, color, salts, U.V. adsorber | q.s. to 100 |

Two or three bottle capfuls of the above lotion held under the tap releasing the water into the bathtub yields a copiously foamed bubble bath with no visible precipitation flocculation, or "bathtub ring" even using hard water. Bathing in this bath is found to have a cleansing and pleasing emollient effect on the skin as described above.

When, after immersion in this bath, the body is soaped, rinsed and dried, an even better, more long-lasting emollient, moisturizing effect on the skin is observed. The foam or bubbles are substantially unaffected by the soaping step, and no precipitate, flocculate or "bathtub ring", or any bothersome film or coating on the bathtub surface is found.

The aroma produced is as set forth in Table II below:

TABLE II

| Product | Aroma Profile |
|---|---|
| Product produced according to Example I, bulked fractions 2-4 consisting of the compounds having the structures: | A floral, chrysanthemum-like and calamus aroma with camphoraceous, green, labdanum-like, castoreum-like and leathery aroma nuances on dry-out and as undertones. |
| Product produced according to Example II, bulked fractions 4-14 consisting of the compounds having the structures: | A jasmine, fruity aroma. |
| Fragrance produced according to Example III. | A leathery, floral and herbal aroma with intense chrysanthemum, calamus, castoreum, labdanum and camphoraceous undertones. |
| Fragrance produced according to Example IV. | A jasmine aroma with fruity undertones. |

EXAMPLE VI

The following formulation is prepared with results in properties and use similar to those described in Example V:

| Ingredients | Parts by Weight |
|---|---|
| "Merquat 100" | 1.0 |
| Cocoamidopropyl dimethyl glycine | 8.0 |
| Myristyl dimethyl amine oxide | 16.0 |
| Perfume ingredient as set forth in Table II of Example V, supra, giving rise to the aroma profiles as set forth in Table II of Example V, supra | 0.8 |
| Water | q.s. to 100 |

The composition is a clear liquid. Its viscosity may be increased by addition of a lauric or myristic diethanolamide or a soluble polyethylene glycol ester such as polyethylene glycol 6000. In addition, this composition may be rendered opaque by addition of stearic monoethanolaide stearate, polyethylene glycol 600 monostearate or a glyco amido stearate such as "Cerasynt 1P".

EXAMPLE VII

The following shampoo is prepared containing the following ingredients;

| Ingredients | Parts by Weight |
|---|---|
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}$-$C_{20}$ fatty acyl monoethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table II of Example V, supra, giving rise to the aroma profiles as indicated in Table II of Example V | 1.0 |
| Deionized water (3 micromhos/cm conductivity) | 46.0 |

A shampoo of the above composition is made in the following matter. First, the tridecyloxy polyethoxy ethanol is added to a clean mixing tank, with the agitator on, and the amine oxide, polyoxyethylene sorbitan monolaurate and cocomonoethanolamine are added sequentially, with continued agitation. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer, the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide, the solution thereof is added to the first mixing tank with agitation and is blended with the nonionics, such mixings being at room temperature. Subsequently, the perfume as indicated in Table II of Example V, supra, giving rise to the aroma profile as set forth in Table II of Example V, supra, is admixed with the balance of the composition and mixing is continued for another half hour.

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml and a foam stability of 60 seconds.

In panel evaluations of the experimental shampoo compared to a different commercial product, in actual shampooing, the experimental formula was adjudged significantly better in being less drying, porducing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE VIII

Fabric Freshener Composition

A fabric freshener composition is prepared as follows:

| Ingredients | Parts by Weight |
|---|---|
| Sodium bicarbonate | 3 |
| "Kyro" EOB (Trademark)* | 1 |
| Perfume ingredient as set forth in Table II of Example V, supra, giving rise to an aroma as set forth in Table II of Example V, supra | 1 |
| Water | 0.05 |

*A commercial nonionic surfactant comprising an average of eleven carbon atoms, ethoxylated to an average of 9 ethyleneoxy groups per molecule.

The composition of this Example is prepared by simply mixing the ingredients.

The above described composition is applied to a lightly soiled and wrinkled fabric as droplets (ca. 5.0 mm avg. size) using a trigger acton sprayer having a nozzle which is adjustable to provide composition droplets in the desired range. The composition is applied at a rate of about 1 gram of composition to about 10 grams of fabric.

The fabric is then placed in an automatic dryer and dried, with tumbling action, at a temperature of 60° C.-80° C. for a period of 15 minutes. The fabric is rendered free of wrinkles and static, and has a fresh appearance and pleasant odor profile as set forth in Table II of Example V, supra. Surprisingly, the sodium bicarbonate is not visible on the refreshed fabric.

In the foregoing procedure, substantially the same results were obtained when sodium carbonate is substituted for the sodium bicarbonate.

EXAMPLE IX

Perfumed Liquid Detergent

Concentrated liquid detergents (lysine salts of n-dodecyl benzene sulfonic acid as more specifically described in U.S. Pat. No. 3,948,818, issued on Apr. 6, 1976) with aromas as indicated in Table II of Example V, supra, are prepared containing 0.10%, 0.15%, 0.20%, 0.25%, 0.30%, 0.40%, 0.50% and 0.80% of the perfume ingredient as set forth in Table II of Example V, supra. The detergents are prepared by adding and homogeneously mixing the appropriate quantity of perfume ingredient as set forth in Table II of Example V, supra. The detergents all possess aromas as set forth in Table II of Example V, supra with the intensity of each increasing with greater concentrations of the perfume ingredient as indicated in Table II of Example V, supra.

EXAMPLE X

Preparation of a Cologne and Handkerchief Perfume

The perfume ingredient as set forth in Table II of Example V, supra is incorporated into colognes at concentrations of 2.0%, 2.5%, 3.0%, 3.5%, 4.0%, 5.0% and 6.0% in 75%, 80%, 85%, 90% and 95% aqueous ethanol solutions. Distinct and definite aromas as set forth in Table II of Example V, supra, are imparted to the colognes. The perfume ingredients as indicated in Table II of Example V, supra, are also added to handkerchief perfumes at concentrations of 15%, 20%, 25% and 35% (in 75%, 80%, 85%, 90% and 95% aqueous ethanol) and aroma profiles as set forth in Table II of Example V, supra, are imparted to the handkerchief perfume.

EXAMPLE XI

Blueberry Flavor Formulation

The following formulation is prepared:

| Ingredients | Parts by Weight |
|---|---|
| Heliotropin | 3.0 |
| Terpinenol-4 (10% in 95% aqueous food grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl hexanoate | 2.0 |
| Hexanal | 1.0 |
| Eucalyptol (1% in 95% aqueous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |
| | 100.0 |

The above formulation is split into 2 portions. To the first portion is added at the rate of 1%, the norbornane derivative prepared according to Example I, a mixture having the structures:

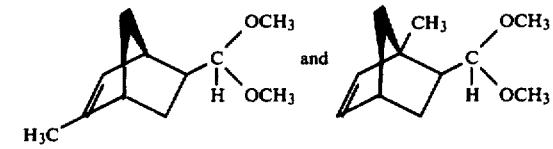

To the second portion nothing is added. The two formulations with and without said norbornyl derivatives are combined with water at the rate of 100 ppm. The flavor of the portion containing the norbornyl derivatives prepared according to Example I has a fruity, blueberry characteristic and is closely similar to the flavor of wild blueberries. It is therefore preferred to use the formulation containing the norbornyl derivative of Example I to the basic blueberry formulation which does not contain said norbornyl derivative.

EXAMPLE XII

Fruited Tapioca Cream

The contents of Ann Page Tapioca pudding mix (ingredients: sugar, corn starch, tapioca, sodium chloride, tapioca flavor and artificial color; Net weight 138 grams) is emptied into a sauce pan. Three cups of milk are added together with one beaten egg yolk previously blended therewith. The resulting mix is cooked over medium heat stirring constantly while slowly adding at the rate of 0.2%, the flavor material of Example XI (blueberry flavor), containing the norbornyl derivatives of Example I. The resulting mixture, after heating, is then cooled to room temperature in the saucepan. One egg white is slowly added to the resulting mixture together with three tablespoons of sugar. The resulting mixture is then blended and chilled yielding pleasantly tasting blueberry tapioca cream dessert.

EXAMPLE XIII

Flavored Instant Pudding

A pudding mix (Royal Instant, net weight 3.5 ozs. produced by Standard Brands, Inc., New York, N.Y. 10022) is intimately admixed with 2 cups of cold fresh whole milk. To this mixture at the rate of 0.3% is added the blueberry flavor of Example XI containing the norbornyl derivatives of Example I. The resulting mixture is blended in a Waring blender for a period of three minutes. The resulting mixture is then cooled at 15° C. for a period of five minutes. The resulting pudding has an excellent natural blueberry flavor.

EXAMPLE XIV

A. Powder Flavor Composition 20 grams of the flavor composition of Example XI (containing the norbornyl derivatives of Example I) is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
|---|---|
| Liquid blueberry flavor composition of Example XI | 20 |

| Ingredients | Parts by Weight |
| --- | --- |
| Propylene glycol | 9 |
| Cab-O-Sil ® M-5 (Brand of silica produced by the Cabot Corp. of 125 High St., Boston, Mass. 02110; Physical properties: Surface area: 200 m²/gm Nominal particle size: 0.012 microns Density: 2.3 lbs/cu. ft. | 5 |

The Cab-O-Sil ® is dispersed in the liquid blueberry flavor composition of Example XI with vigorous stirring, thereby resulting in a viscous liquid. 71 parts by weight of the powder flavor composition of Part A, supra, is then blended into the said viscous liquid, with stirring, at 25° C. for a period of 30 minutes resulting in a dry, free flowing, sustained release flavor powder.

EXAMPLE XV 10 parts by weight of 50 Bloom pigskin gelatin is added to 90 parts by weight of water at a temperature of 150° F. The mixture is agitaged until the gelatin is completely dissolved and the solution is cooled to 120° F. 20 parts by weight of the liquid flavor composition of Example XI (containing norbornyl derivatives of Example I) is added to the solution which is then homogenized to form an emulsion having particle size typically in the range of 2–5 microns. This material is kept at 120° F. under which conditions the gelatin will not jell.

Coacervation is induced by adding, slowly and uniformly, 40 parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XVI 100 parts by weight of chicle are mixed with 4 parts by weight of the flavor prepared in accordance with Example XIV. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting, blueberry flavor.

EXAMPLE XVII

Chewing Gum 100 parts by weight of chicle are mixed with 18 parts by weight of the flavor prepared in accordance with Example XV. 300 parts of sucrose and 100 parts of corn syrup are then added. Mixing is effected in a ribbon blender with jacketed side walls of the type manufactured by the Baker Perkins Co.

The resulting chewing gum blend is then manufactured into strips 1 inch in width and 0.1 inches in thickness. The strips are cut into lengths of 3 inches each. On chewing, the chewing gum has a pleasant, long-lasting, blueberry flavor.

EXAMPLE XVIII

Toothpaste Formulation

The following separate groups of ingredients are prepared:

| Parts by weight | Ingredients |
| --- | --- |
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalsium phosphate (dihydrate) |
| Group "C" | |
| 2.000 | Sodium n-lauroyl sarcosinate (foaming agent) |
| Group "D" | |
| 1.200 | Flavor material of Example XIV |
| 100.000 total | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure, yields a pleasant blueberry flavor of constant strong intensity throughout said procedure (1–1.5 minutes).

EXAMPLE XIX

Chewable Vitamin Tablets

The flavor material of Example XIV is added to a chewable vitamin tablet formulation at the rate of 10 gm/kg which chewable vitamin tablet formulation is prepared as follows:

In a Hobart Mixer, the following materials are blended to homogeneity:

| | Gms/1000 Tablets |
| --- | --- |
| Vitamin C (ascorbic acid) as ascorbic acid-sodium ascorbate mixture 1:1 | 70.00 |
| Vitamin B₁ (thiamine mononitrate) 33⅓% (Hoffman La Roche) | 4.0 |
| Vitamin B₂ (roboflavin) as Rocoat ® roboflavin 33⅓% | 5.0 |
| Vitamin B₆ (pyridoxine hydrochloride) as Rocoat ® pyridoxine hydrochloride 33⅓% | 4.0 |
| Niaminamide as Rocoat ® niacinamide | |

-continued

| | Gms/1000 Tablets |
|---|---|
| 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XIV | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 grams dry Vitamin A Acetate and 0.6 grams Vitamin D are then added as beadlets. The entire blend is then compressed using concave punches at 0.5 grams each.

Chewing of the resultant tablets yields a pleasant long-lasting, consistently strong blueberry flavor for a period of 12 minutes.

EXAMPLE XX

Chewing Tobacco

Onto 100 pounds of tobacco for chewing (85% Wisconsin leaf and 15% Pennsylvania leaf) the following casing is sprayed at a rate of 30%:

| Ingredients | Parts by weight |
|---|---|
| Corn syrup | 60 |
| Licorice | 10 |
| Glycerine | 20 |
| Fig juice | 4.6 |
| Prune juice | 5 |
| Flavor material of Example XI containing the norbornyl derivatives of Example I | 0.4 |

The resultant product is redried to a moisture content of 20%. On chewing, this tobacco has an excellent substantially consistent, long-lasting blueberry nuance in conjunction with the tobacco note.

EXAMPLE XXI

"Pina Colada" Beverage

An alcoholic beverage is prepared by mixing the following ingredients in a Waring Blender for 4 minutes:

| Ingredient | Parts by Weight |
|---|---|
| Natural coconut milk | 400 |
| Coconut meat | 1,280 |
| Vodka (SMIRNOFF ®) | 480 |
| Papaya fruit meat | 85 |
| Mango nectar | 85 |
| Norbornyl derivative mixture of Example II, bulked fractions 4–14 containing the compounds having the structures: | 7 |

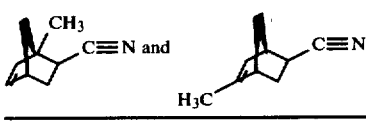

The norbornyl derivatives of Example II add an intense, pleasant "natural cooked coconut" nuance to this "pina colada" beverage. Surprisingly, on standing in the presence of cooling ice at a temperature of 32° F. for a period of 6 hours, the original freshness of the pina colada beverage remains.

What is claimed is:

1. The process for augmenting or enhancing the aroma of a perfume composition or cologne comprising the step of adding to a perfume base or a cologne base at lease one compound defined according to the structure:

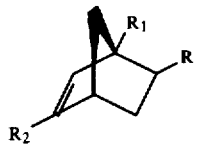

wherein R represents the nitrile moiety having the structure:

or the dimethoxymethyl moiety having the structure:

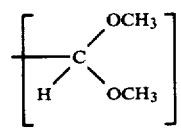

and wherein one of R$_1$, or R$_2$ is methyl and the other of R$_1$ or R$_2$ is hydrogen.

* * * * *